United States Patent
Walte et al.

(10) Patent No.: US 8,586,383 B2
(45) Date of Patent: Nov. 19, 2013

(54) DEVICE AND METHOD FOR DETECTION OF HARMFUL SUBSTANCES

(75) Inventors: Andreas Walte, Schwerin (DE); Wolf Münchmeyer, Ehra-Lessien (DE)

(73) Assignee: Airsense Analytics, Schwerin (DE)

( * ) Notice: Subject to any disclaimer, the term of this patent is extended or adjusted under 35 U.S.C. 154(b) by 34 days.

(21) Appl. No.: 13/107,361

(22) Filed: May 13, 2011

(65) Prior Publication Data

US 2011/0281367 A1    Nov. 17, 2011

(30) Foreign Application Priority Data

May 17, 2010    (EP) .................................... 10162947

(51) Int. Cl.
*G01N 1/22*    (2006.01)
*G01N 33/00*    (2006.01)
*G01N 31/00*    (2006.01)

(52) U.S. Cl.
USPC ........... 436/181; 436/124; 436/119; 436/120; 436/130; 436/134; 436/140; 436/141; 436/142; 436/106; 436/113; 436/103; 422/83; 422/98; 73/23.2

(58) Field of Classification Search
USPC ............... 436/43, 91, 93, 124, 119, 120, 127, 436/128, 130, 133, 134, 139, 140, 141, 142, 436/106, 109, 113, 103, 104, 149, 151, 164, 436/167, 181; 422/400, 401, 403, 416, 83, 422/88, 90, 91, 98; 73/23.2
See application file for complete search history.

(56) References Cited

U.S. PATENT DOCUMENTS

| 4,670,405 A | 6/1987 | Stetter et al. |
| 5,356,594 A * | 10/1994 | Neel et al. ......................... 422/54 |
| 5,821,405 A | 10/1998 | Dickey et al. |
| 6,996,478 B2 * | 2/2006 | Sunshine et al. ................. 702/22 |
| 2002/0178789 A1 | 12/2002 | Sunshine et al. |
| 2011/0015875 A1 * | 1/2011 | Walte et al. ...................... 702/24 |

FOREIGN PATENT DOCUMENTS

| DE | 38 22 022 A1 | 1/1990 |
| EP | 0 345 568 A2 | 12/1989 |
| GB | 2 155 185 A | 9/1985 |
| GB | 2 239 952 A | 7/1991 |
| WO | 2009/112001 * | 9/2009 |

* cited by examiner

*Primary Examiner* — Maureen Wallenhorst
(74) *Attorney, Agent, or Firm* — Norris McLaughlin & Marcus PA

(57) ABSTRACT

The invention relates to a device (10) for detection of harmful substances with a measurement unit (28) for measuring at least one harmful substance and an evaluation unit (30) for determining the concentration of the at least one harmful substance. The invention also relates to a method for detecting harmful substances in a gas mixture. It is hereby provided that the gas mixture is tested for a gaseous harmful substance or simultaneously for several gaseous harmful substances, wherein the gaseous harmful substance or the gaseous harmful substances is/are measured with different sensor means, and the gaseous harmful substances are optionally chemically modified such that a measurement is performed with the existing sensor means.

18 Claims, 3 Drawing Sheets

DEVICE AND METHOD FOR DETECTION OF HARMFUL SUBSTANCES

The invention relates to a device and a method for detection of harmful substances, wherein a gas mixture is tested for the presence of gaseous harmful substances.

It is known to use fumigants for pest control of buildings, also for individual furnishings of buildings, as well as in food processing plants, for example in storage spaces, transport containers (container). Use of these fumigants makes an effective control of pests possible, because the fumigant reaches almost every location due to its uniform distribution in the room where the pests to be controlled reside. After a certain exposure time of the fumigant, the rooms and objects or products to which the fumigant is exposed are ventilated. However, it cannot be ensured in every situation that the ventilation is adequate. As a result, residues of the fumigant may still be in the buildings or transport containers. Persons entering the buildings or intending to empty or control the transport container would then be exposed to a health hazard.

Fumigants are, for example, gaseous harmful substances containing sulfur, chlorine and/or phosphorus.

U.S. Pat. No. 4,670,405 discloses a portable device with a number of sensors capable of detecting different gaseous harmful substances in a gas mixture. The sensors are here designed for standard harmful substances to be detected. Harmful substances which do not correspond to the standard harmful substances or harmful substances having no sensor elements available for their detection can therefore not be detected with this device.

It is an object of the invention to provide a method and a device of the generic type, which is capable of readily detecting gaseous harmful substances, in particular when these are present in different combinations and in small concentrations even in the presence of other substances.

According to the invention, this object is solved with a device having the features recited in claim 1. Advantageously, the device can be readily adapted to different measurement situations by providing the device with a detection unit for detecting at least one harmful substance and an evaluation unit for determining the concentration of the at least one harmful substance, wherein the detection unit includes at least two sensor means for simultaneously measuring different harmful substances, and the sensor means are arranged to be interchangeable and reversibly connectable with the evaluation unit. In particular, the device is distinguished by a high variability.

In a preferred embodiment of the invention, the sensor means are interchangeably arranged with a plug-in connection or the like which, in particular, simplifies handling. The sensor means themselves include preferably a microcontroller system configured to perform automatic calibration and contacting with the evaluation unit. An operator can then readily interchange the sensors on-site, thereby obviating the need for complex adjustments or calibrations of the entire device.

According to another preferred embodiment of the invention, the device includes a modulator or can be combined with a modulator for decomposing detected harmful substances into measurable chemical substances. In this way, gaseous harmful substances which cannot be detected with the available sensor means can advantageously be modified so that a gaseous substance is produced as a transformation and/or decomposition product which can be detected with the existing sensor means. This significantly enhances the applicability of the device. In particular, all common gaseous harmful substances can then be detected in a simple and rapid fashion, even those substances for which special sensor means are not available. With this indirect determination of the harmful substances, the device can then be used over a much greater spectrum of applications.

In addition, in a preferred embodiment of the invention, combinations of different gas sensors, for example electrochemical cells and/or photo ionization detectors and/or NDIR sensors and/or metal oxide sensors and/or pellistors and/or ion mobility spectrometers can be used as sensor elements for detecting gaseous compounds. For realizing a portable and small device, preferably small sensors, such as electrochemical cells and/or photo ionization detectors and/or NDIR sensors and/or metal oxide sensors and/or pellistors are used. Optionally, a gamma ray detector can be used for detecting radioactive radiation. In this way, the device can be variably adapted to the concrete measurement task. With the different sensor means, the presence of several harmful substances can be simultaneously and reliably detected.

In addition, a preferred embodiment of the invention, the device may include a communication unit for communication with a test object and/or a central computer, wherein a transmission link between the device and the central computer is preferably established wirelessly via radio, WLAN, Bluetooth or wired via a USB interface. A communication with the test object can be established, for example, via optical scanners or via passive wireless methods, such as RFID, or active methods, such as WLAN, Bluetooth or ZigBee. The device can then be universally employed and can be flexibly used on complex terrain, for example when examining and controlling transport containers (containers) in large port facilities and the like.

The object is also solved with a method having the features recited in claim 13. Advantageously, complex measurements of gas mixtures for several gaseous harmful substances, which may be present in small concentrations, can be performed with high selectivity by testing the gas mixture for at least one harmful substance, wherein at least one gaseous harmful substance is detected with different sensor means and optionally the gaseous substance is chemically modified such that detection is performed with the existing sensor means, wherein preferably the gas mixture is simultaneously tested for at least two gaseous harmful substances, wherein the at least two gaseous harmful substances are detected with different sensor means and optionally the gaseous harmful substances are chemically modified such that detection is performed with the available sensor means. In particular, the gas mixture may be suctioned from a closed space, for example a transport container, with a probe or the like and supplied to the device of the invention. Due to the modulation, chemical compounds can be periodically decomposed and supplied to different sensor means, for example electrochemical sensors and/or photo ionization detectors. The measurement result in the reaction of a single harmful substance can be verified by using several sensors.

In another preferred embodiment of the invention, information about a test object to be tested can be used before the chemical analysis of the gas mixture in order to tune the chemical analysis to the expected substances. For example, if a container with a particular merchandise, for example shoes, is to be tested, a corresponding database with a listing of the most likely occurring gaseous harmful substances can be loaded. In this way, the accuracy and information content of the measurement can be enhanced. In particular, the device can be sensitized to experience-based expected or feared harmful substances.

In a particular embodiment of the invention, the information about the test object may be received wirelessly, the results of the analysis may be temporarily stored and the results of the analysis may be transmitted to a central computer. This approach advantageously ensures a continuous documentation chain and consequently also with a high degree of confidence the identification or lack of identification of harmful substances in the measured test objects, for example buildings or transport containers.

In addition, in another preferred embodiment of the invention, the gas mixture is transported across a photo ionization detector for the detection of benzene, toluene, styrene, carbon disulfide, trans-1,2-dichloro-ethene, methylene bromide and dibromomethane as well as phosphine, ammonia and ethylene oxide; the gas mixture is transported across the at least one electrochemical cell for the detection of hydrogen cyanide and phosphine; the gas mixture is transported across an additional electrochemical cell for the detection of formaldehyde; the gas mixture is transported across an additional electrochemical cell for the detection of carbon monoxide. For the detection of a gaseous compounds which are not detected by these sensors, for example sulfuryldifluoride, chlorpicrin, carbonylsulfide and chlormethane, the gas mixture is transported across a modulator which generates decomposition and/or transformation products, and the decomposition and/or transformation products are transported across an additional electrochemical cell or additional electrochemical cells. Alternatively, the gaseous compounds which are not detected by these sensors, but are detected through interaction of the decomposition and/or transformation products, can also be detected with the other electrochemical cells. In this way, very different gaseous harmful substances can advantageously be identified simultaneously with the device on a large scale, and corresponding warning signals can be generated.

In a preferred embodiment of the invention, the detectability can be increased by comparing a response from all sensor means of the device with an unactivated modulator and the response from all sensor means with an activated modulator with the results from previous measurements and by producing an alarm signal in the event of a positive identification based on mathematical methods, for example a pattern recognition method. This allows immediate verification of the measurement on-site, i.e. on the test object, which increases the accuracy of the measurement results.

In addition, in another preferred embodiment of the invention, an operator guide is provided by the device before the actual measurement process by indicating the individual steps in the measurement process flow so as to prevent operating errors. This may take the form of, for example, a representation on a display or an acoustic signal, and can relate to sequential reading of specific information relating to the test object and its content, respectively, to reading data of the operator, to inserting a probe into the test object, as well as to the determined results of the measurement and the required steps which must be performed for combining the information from the measurement results and to setting up predefined protocols. This ensures a very precise measurement with high information content.

Lastly, in another preferred embodiment of the invention, one-handed control and handling may be enabled, by combining the measuring probe and the device into a single unit or by connecting the measuring probe with a device via a hose and carrying the device on the body.

Additional preferred embodiments of the invention can be inferred from the other features recited in the dependent claims.

Exemplary embodiments of the invention will now be described in more detail with reference to the appended drawings, in which.

Figure 1:
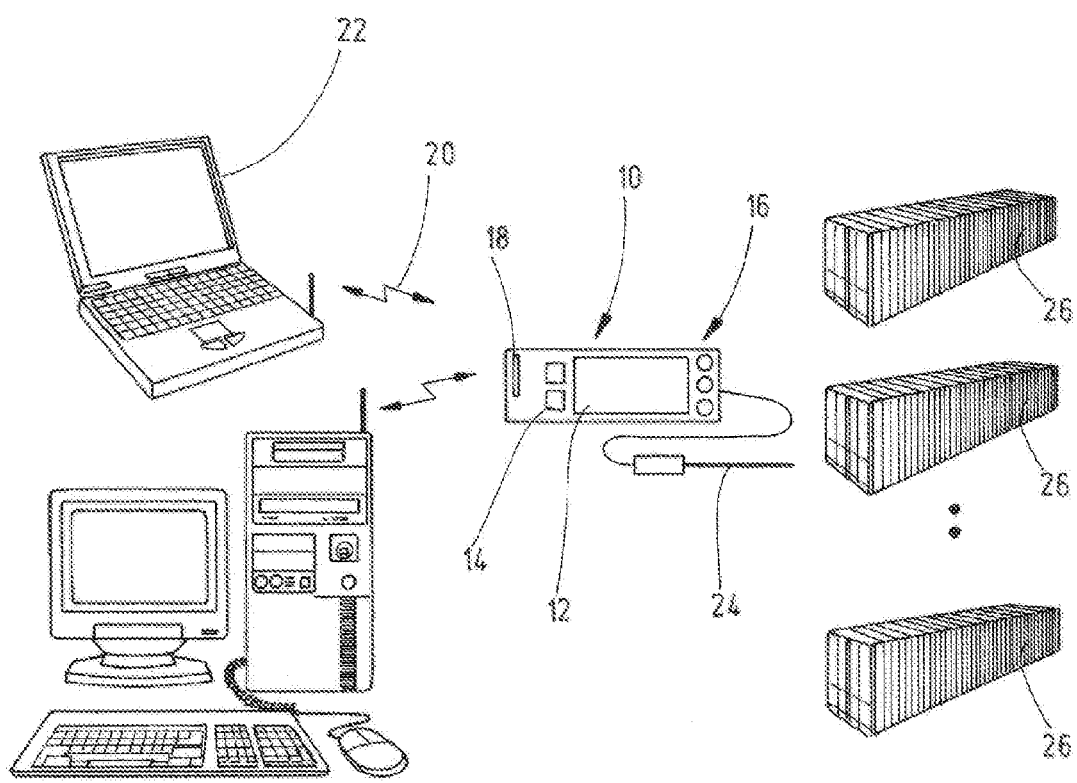
FIG. 1 shows schematically the use of a device according to the invention.

FIG. 1 shows a schematic overall view for using a device 10 according to the invention. The device 10 is suitable for detecting harmful substances and is constructed as a portable handheld device. The device 10 includes a display 12 and control means 14 configured for controlling the device 10 or the menus for the device 10. The device 10 also includes an indicator device 16 for displaying a measurement status. Also provided is an interface 18 for setting up a transmission link 20 to or from a computer 22, laptop and the like. The transmission link 20 can be implemented via radio, WLAN, Bluetooth, USB connection and the like.

The device 10 further includes a measuring probe 24 adapted for a connection to an interior space of the indicated transport container 26. The measuring probe 24 can be inserted, for example, through seals of the transport container 26, thereby providing a connection between the interior space of the transport container 26 and the surroundings only through the measuring probe 24, thereby preventing exposure of the operator to the air inside the transport container 26.

The device 10 also includes an (unillustrated) power supply, for example a rechargeable battery.

The device 10 also includes—as will be discussed in more detail below—various sensor means for detecting different gaseous harmful substances, which can be used to detect the composition of the gas mixture inside the transport container 26. Accordingly, the presence of one or more gaseous harmful substances inside the transport container 26 can be determined with the device 10, which would otherwise endanger people and the surroundings if the transport container 26 were opened or entered.

The device 10 illustrated in FIG. 1 shows the following general functionality:

After the device is switched on, the user is asked for identification and requested to enter the identification. This can be performed via suitable menu navigation via control elements 14. Thereafter, information about the forthcoming measurements is entered into the device 10. These may be, for example, codes of the transport container to be measured, information about the goods contained in the transport containers 26, point of origin or destination of the transport container 26 and the like. For simplifying input on this information, the device 10 may be equipped with a barcode scanner configured to read out barcodes arranged on the transport container 26. The device 10 may also be equipped with a digital camera or the device 10 may be connected with a digital camera via a data link (USB, WLAN, Bluetooth and the like) for documenting the transport container 26. The device may also be equipped with a microphone to enable voice-controlled menu navigation. The device 10 is hence provided with all relevant initial information for the measurement to be performed. This initial information is stored in a memory of the device 10. This memory can be a permanent memory or a removable memory (USB stick, SD card and the like).

The device 10 is subsequently operational, whereby the measurement can be started with a suitable start command, for example via menu navigation or with a start key. The measuring probe 24 is inserted into the interior space of a first transport container 26. The start of the measurement can be indicated to the operator by an acoustic message or corresponding information on the display 12. Likewise, the end of the measurement may be indicated via an additional acoustic signal or a change in the indication on the display 12. The device 10 then automatically performs the test for gaseous harmful substances inside the transport container 26, as will be described below. The corresponding measurement data are temporarily stored on the aforementioned memory in the device 10 and associated with the corresponding output information of the measurements, such as the code of the transport container, etc.

The device 10 then performs a first evaluation of the determined measurement data, thereby providing the user quickly with qualitative information. The indicator device 16 optically indicates if the transport container 26 contains one or even several gaseous harmful substances. The indicator device 16 may have at least one light emitting diode which signals to the user qualitative information by way of a different blinking frequency or a different color. For example, a green display may indicate that the evaluation of the measurement has shown that no alarm value was reached or exceeded. All measurement values are significantly below the alarm values. A yellow display may signal that the evaluation of the measurement has shown that predetermined alarm values have been reached for individual substances to be tested, but have not been exceeded. Finally, a red signal may indicate that the evaluation of the measurement has shown that at least one of the detected substances has exceeded a maximum occupational exposure limit (AGW value, which corresponds to the earlier MAK value). The corresponding threshold values, where alarm is triggered or is almost triggered, can be fixedly programmed into the device 10 for recurring measurements of certain substances. It is also possible to adapt individual values for certain substances to be detected via the menu navigation on the device 10.

At the termination of the measurement on a transport container or after termination of a measurement series on several transport containers 26, the corresponding measurement results can be transmitted via the transmission link 20 to a computer or the like, where they are archived in a database. In addition, the determined measurement results can be analyzed in detail, for example by displaying and evaluating measurement spectra and the like. Thereafter, the information and measurement results associated with the individual transport containers 26 are documented and archived.

Figure 2:
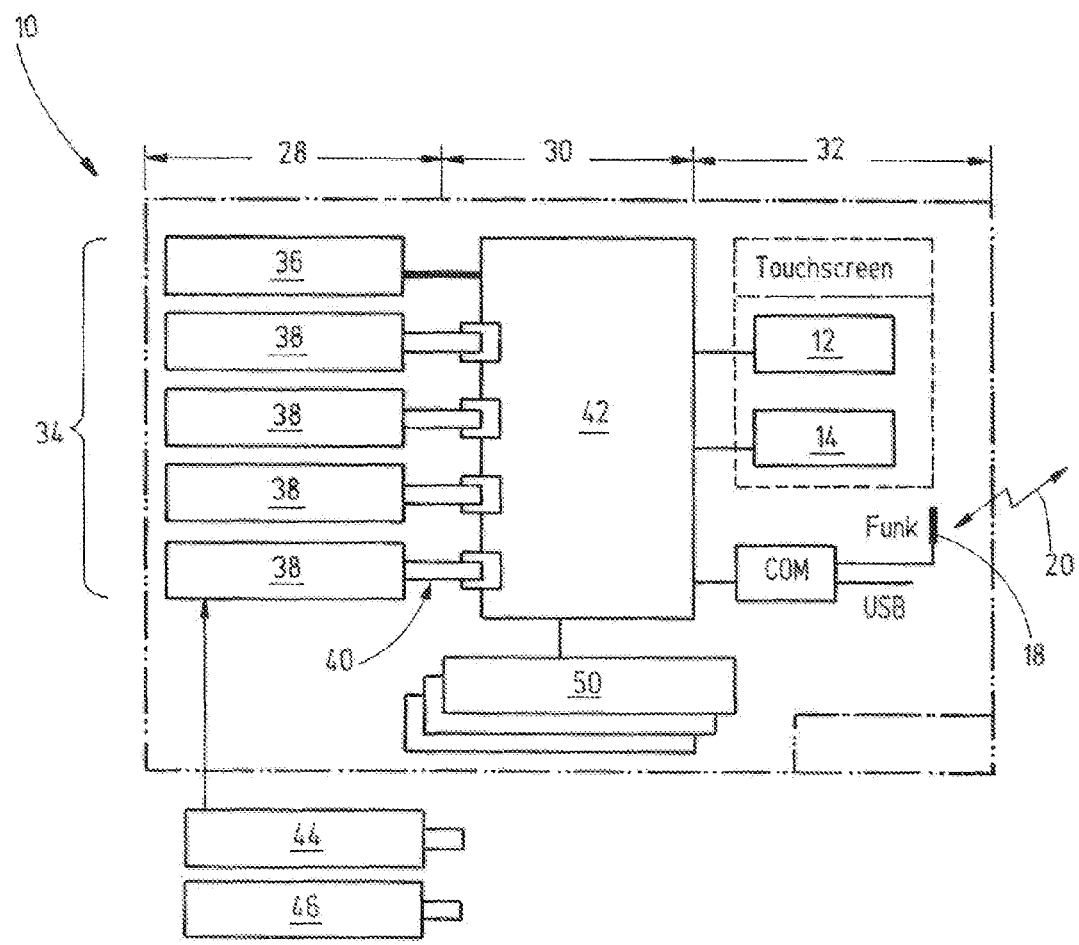
FIG. 2 shows a schematic block diagram of the device according to the invention in a first exemplary embodiment.

FIG. 2 shows a schematic block diagram of the device 10. As clearly seen, the device 10 includes a measurement unit 26, an evaluation unit 30 and a communication unit 32.

The measurement unit 28 has several sensor elements 34, with one of the sensor elements 34 being implemented as a photo ionization detector 36. The other sensor elements are embodied, for example, as electrochemical cells 38. The electrochemical cells 38 are connected with the evaluation unit 30 by way of reversible plug connections 40. Microcontroller systems (for example PIC controllers) of the corresponding electrochemical cells 38 are contacted via the plug connections 40 with a microprocessor or microcontroller 42 of the evaluation unit 30. The microcontroller of the respective electrochemical cells 38 allows storage of relevant data, for example the corresponding manufacturing data, expiration date and the calibration parameters. An automatic adaptation or adjustment of the electrochemical cells 38 is performed with this contact connection between the electrochemical cells 38 and a microprocessor 42. The design of the plug connections 40 allows interchange of the electrochemical cells 38. For example, the interchange may be performed to equip the device 10 with different electrochemical cells 38 commensurate with the desired or expected measurement task. A flexible response to different measurements of gaseous harmful substances with a device 10 is then possible. Moreover, potentially defective electrochemical cells 38 can then also be readily exchanged.

FIG. 2 indicates that the electrochemical cells 38 can also be interchanged, for example, with other sensor elements 44 and 46, respectively. This allows a flexible response to different measurement task.

For example, solvents can be detected with the PID sensor 36. All molecules with an ionization potential smaller than the energy of the UV radiation are ionized with UV radiation. The generated ions are detected on two electrodes by applying a voltage. This allows excellent detection of relevant substances, for example benzene, toluene, styrene, carbon disulfide, trans-1,2-dichlorethene, methyl bromide and/or dibromomethane. phosphine. Ammonia and ethylene oxide can also be detected.

A total of four electrochemical cells 38 provided in the exemplary embodiment is used for the detection of phosgene with cross sensitivity to phosphine, arsine, hydrogen cyanide, hydrochloric acid and hydrogen sulfide. The detection limit for phosphine or hydrogen cyanide is, for example, between 0.1 and 0.5 ppm. An additional electrochemical cell 38 can be used to detect formaldehyde, with cross sensitivity to carbon monoxide, ethanol and methanol. The detection limit is, for example, 1 ppm. An additional electrochemical cell 38 can be used to detect sulfur dioxide. A detection limit is, for example, 1 to 2 ppm. Lastly, an additional electrochemical cell 38 can be used for the detection of carbon monoxide with cross sensitivities to ethanol, hydrogen cyanide, hydrogen and sulfur dioxide. The detection limit is here for example 20 ppm.

The indicated interchange sensor 44 can be used, for example, for the detection of carbon dioxide with an NDIR (non-dispersive infrared) sensor. A detection limit is for example 1000 ppm. Lastly, the sensor element 46 can be used for the detection of gamma radiation, thus optionally allowing the detection of any existing radioactivity.

The interchange sensors may also be formed, for example, by metal oxide sensors and/or IR absorption cells and/or pellistors, or may also have in other exemplary embodiments a more complex design, for example ion mobility spectrometers.

Figure 3:
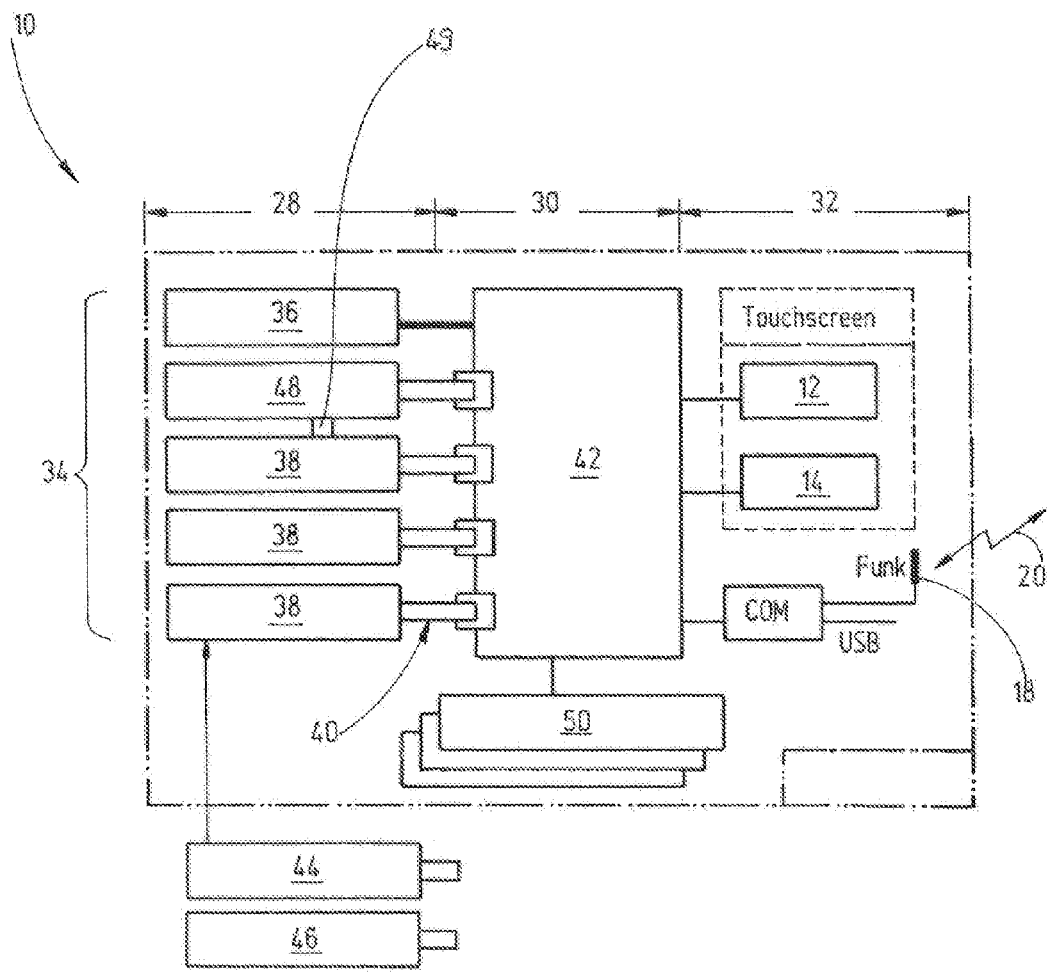
FIG. 3 shows a schematic block diagram of the device according to the invention in a second exemplary embodiment.

FIG. 3 shows a device 10 with a structure that is different from the exemplary embodiment illustrated in FIG. 2. The same elements as in FIG. 2 have identical reference symbols and will not be described again. Instead of a sensor element 38, a modulator 48 is here provided which is also interchangeably arranged on the device 10. The modulator 48 is connected with at least one of the sensor elements 38 via a gas-conducting connection 49. However, the modulator 48 may also be placed upstream of all or of several sensor elements.

In this way, components in the gas mixture to be detected can be decomposed with the modulator 48 into decomposition or transformation products, which can then be detected with the sensor elements 38. This particularly applies to those gaseous harmful substances which cannot be detected directly by using the sensor elements 38, 44 and 46, respectively. For example, sulfuryl difluoride $SO_2F_2$ may be decomposed with a modulator 48 into the transformation product sulfur dioxide $SO_2$ which can then be detected with the sensor element 38 embodied as an electrochemical measurement cell.

The device illustrated in both FIG. 2 and FIG. 3 includes the evaluation unit 30, with which the central microprocessor 42 is associated. Additional information of the device 10 may be stored by way of a memory expansion 50. The memory expansion 50 may be formed, for example, by an interchangeable memory, for example a USB stick, SD cards and the like. In this way, different measurement tasks can be variably assigned to the device 10, which are then transmitted via the central microprocessor 42 to the microcontrollers in the individual sensor elements and the modulator, respectively, by way of the plug-in connections 40. On the other hand, the data obtained from the measurement can be stored with the memory expansion 50. With the interchangeable memory means, the device 10 can be easily reconfigured for different measurement tasks. Due to the interchangeability of the sensor elements 38, 44, 46 and of the modulator 48 and the memory means 50, respectively, a flexible and quick reaction to changing measurement tasks becomes possible.

The device also includes the communication unit 32, with which the display 12 and the control means 14 are associated. The transmission link 20, for example to a central computer 22, is set up via the interface 18.

List of References Symbols

10 Device
12 Display
14 Control means
16 Display device
18 Interface
20 Transmission link
22 Computer, laptop or the like
24 Measuring probe
26 Transport container
28 Measurement unit
30 Evaluation unit
32 Communication unit
34 Sensor elements
36 Photo ion detector/PID sensor
38 Electrochemical cells
40 Plug-in connections
42 Microprocessor, microcontroller
44 Sensor elements, interchangeable sensor
46 Sensor elements
48 Modulator
49 Connection
50 Memory expansion

The invention claimed is:

1. Device (10) for detection of harmful substances in a gas mixture comprising a measurement unit (28) for measuring at least one harmful substance and an evaluation unit (30) for determining the concentration of the at least one harmful substance, wherein the measurement unit (28) comprises at least two sensor elements (34) for simultaneous measurement of different harmful substances, and the sensor elements (34) are interchangeably arranged and reversibly connectable with the evaluation unit, wherein the sensor elements (34) comprise a microcontroller system by which the sensor elements (34) are contacted with the evaluation unit (30), and are interchangeably connected by way of a plug-in connection (40) and wherein the device comprises a modulator (48) for decomposition of detected harmful substances into measurable chemical substances.

2. Device according to claim 1, wherein electrochemical cells (38) and/or photo ion detectors (36) and/or NDIR sensors (44) and/or radioactivity sensors (46) are used as sensor elements (34).

3. Device according to claim 2, wherein that in addition to the electrochemical cells (38) and/or photo ion detectors (36) and/or NDIR sensors (44) and/or radioactivity sensors (46), an ion mobility spectrometer is used as a sensor element (34).

4. Device according to claim 1, wherein a communication unit (32) is provided for communication with a test object (26) and/or a central computer (22).

5. Device according to claim 4, wherein a transmission link (20) between the device (10) and the central computer (22) is implemented wirelessly.

6. Device according to claim 1, wherein the device (10) comprises a barcode scanner or an RFID reading device.

7. Device according to claim 1, wherein the device (10) comprises voice control.

8. Device according to claim 1, wherein the device (10) is provided with straps, so that the device (10) can be carried on the body.

9. Device according to claim 8, wherein the device (10) forms a single unit with the measuring probe (24), thus allowing one-handed operation.

10. Method for detecting harmful substances in a gas mixture, comprising testing the gas mixture for at least one harmful substance with the device according to claim 1, whereby at least one gaseous harmful substance is measured with the at least two sensor elements (34) and the gaseous harmful substance is optionally chemically modified with the modulator so as to enable a measurement using the at least two sensor elements (34).

11. Method according to claim 10, wherein the gas mixture is simultaneously tested for at least two gaseous harmful substances, wherein the at least two gaseous harmful substances are measured with the at least two sensor elements (34) and the gaseous harmful substances are optionally chemically modified with the modulator (48) so as to enable a measurement using the at least two sensor elements (34).

12. Method according to claim 10, wherein information about a test object (26) is received wirelessly, results of an analysis are temporarily stored and information and the results of the analysis are transmitted to a central computer (22).

13. Method according to claim 10, wherein operator guidance for eliminating operating errors is implemented in a display such that individual steps in a measurement process flow are indicated before the actual measurement.

14. Method according to claim 10, wherein for increasing the detectability, a response from all of the at least two sensors elements (34) when the modulator (48) is not activated, and a response from all of the at least two sensor elements (34) when the modulator (48) is activated, is compared with results from previous measurements stored in a database.

15. Method according to claim 10 wherein the at least two sensor elements are photo ionization detectors, and a gas mixture is transported across the photo ionization detector for the detection of benzene, toluene, styrene, carbon disulfide, trans-1,2-dichloroethene, methylene bromide and dibromomethane, phosphine, ammonia and ethylene oxide.

16. Method according to claim 10 wherein the gas mixture is transported across at least one electrochemical cell for the detection of hydrogen cyanide and phosphine.

17. Method according to claim 16 wherein the gas mixture is transported across an additional electrochemical cell for the detection of formaldehyde and carbon monoxide.

18. Method according to claim 10 wherein the gas mixture is transported across the modulator (48) which generates decomposition products, and sulfuryldifluoride is measured from its decomposition product ($SO_2$) with an electrochemical cell for the detection of sulfuryl difluoride, chloropicrin, carbonyl sulphide and chloromethane.

* * * * *